United States Patent
Delaney

(10) Patent No.: US 8,992,513 B2
(45) Date of Patent: Mar. 31, 2015

(54) ENDOVASCULAR PLASMA TREATMENT DEVICE AND METHOD OF USE

(75) Inventor: Kevin L. Delaney, Clifton Park, NY (US)

(73) Assignee: AngioDynamics, Inc, Latham, NY (US)

( * ) Notice: Subject to any disclaimer, the term of this patent is extended or adjusted under 35 U.S.C. 154(b) by 276 days.

(21) Appl. No.: 13/539,523

(22) Filed: Jul. 2, 2012

(65) Prior Publication Data
US 2013/0006229 A1    Jan. 3, 2013

Related U.S. Application Data

(60) Provisional application No. 61/503,192, filed on Jun. 30, 2011, provisional application No. 61/559,172, filed on Nov. 14, 2011.

(51) Int. Cl.
| | |
|---|---|
| *A61B 18/14* | (2006.01) |
| *A61B 18/18* | (2006.01) |
| *A61B 18/22* | (2006.01) |
| *A61B 18/04* | (2006.01) |
| *A61B 18/24* | (2006.01) |
| *A61B 18/00* | (2006.01) |

(52) U.S. Cl.
CPC ........... *A61B 18/042* (2013.01); *A61B 18/1492* (2013.01); *A61B 18/245* (2013.01); *A61B 2018/00404* (2013.01); *A61B 2018/00577* (2013.01); *A61B 2018/00613* (2013.01); *A61B 2018/1861* (2013.01)
USPC ............ 606/15; 606/33; 606/41; 604/21; 604/509; 600/300

(58) Field of Classification Search
USPC ................... 606/15, 33; 604/21; 600/300
See application file for complete search history.

(56) References Cited

U.S. PATENT DOCUMENTS

| | | | | |
|---|---|---|---|---|
| 5,275,622 A | * | 1/1994 | Lazarus et al. | 623/1.11 |
| 2009/0018486 A1 | * | 1/2009 | Goren et al. | 604/21 |

* cited by examiner

*Primary Examiner* — Carl H Layno
*Assistant Examiner* — Jon Eric C Morales
(74) *Attorney, Agent, or Firm* — Peter J. Flora

(57) ABSTRACT

A device and method for treating a hollow anatomical structure using matter in a plasma state. Device includes a tubular delivery device comprising a tubular body, a hub, and a distal end, wherein the tubular body device having a longitudinal fluid delivery channel and an exit port near the distal end. Device also contains a container having pre-plasma matter being operatively coupled to the hub, at least one energy-emitting element operatively coupled near the distal end of the tubular delivery device. The energy-emitting element is operatively connected to energy source.

16 Claims, 4 Drawing Sheets

ENDOVASCULAR PLASMA TREATMENT DEVICE AND METHOD OF USE

CROSS REFERENCE TO RELATED APPLICATIONS

This application claims the benefit of U.S. Provisional Application No. 61/503,192, filed Jun. 30, 2011, and U.S. Provisional Application No. 61/559,172, filed Nov. 14, 2011, both which are incorporated herein by reference.

BACKGROUND

Veins are thin-walled and contain one-way valves that control blood flow. Normally, the valves open to allow blood to flow into the deeper veins and close to prevent back-flow into the superficial veins. When the valves are malfunctioning or only partially functioning, however, they no longer prevent the back-flow of blood into the superficial veins. As a result, venous pressure builds at the site of the faulty valves. Because the veins are thin walled and not able to withstand the increased pressure, they become what are known as varicose veins which are veins that are dilated, tortuous or engorged.

In particular, varicose veins of the lower extremities is one of the most common medical conditions of the adult population. It is estimated that varicose veins affect approximately 40% of adult females and 25% of males. Symptoms include discomfort, aching of the legs, itching, cosmetic deformities, and swelling. If left untreated, varicose veins may cause medical complications such as bleeding, phlebitis, ulcerations, thrombi and lipodermatosclerosis.

Traditional treatments for varicosities include both temporary and permanent techniques. Temporary treatments involve use of compression stockings and elevation of the diseased extremities. While providing temporary relief of symptoms, these techniques do not correct the underlying cause, that is the faulty valves. Permanent treatments include surgical excision of the diseased segments, ambulatory phlebectomy, and occlusion of the vein through chemical or thermal means.

Surgical excision requires general anesthesia and a long recovery period. Even with its high clinical success rate, surgical excision is rapidly becoming an outmoded technique due to the high costs of treatment and complication risks from surgery. Ambulatory phlebectomy involves avulsion of the varicose vein segment using multiple stab incisions through the skin. The procedure is done on an outpatient basis, but is still relatively expensive due to the length of time required to perform the procedure.

Chemical occlusion, also known as sclerotherapy, is an in-office procedure involving the injection of an irritant chemical into the vein. The chemical acts upon the inner lining of the vein walls causing them to occlude and block blood flow. Although a popular treatment option, complications can be severe including skin ulceration, anaphylactic reactions and permanent skin staining. Treatment is limited to veins of a particular size range. In addition, there is a relatively high recurrence rate due to vessel recanalization.

Endovascular ablation therapy is another alternative treatment technique for venous reflux diseases. Common forms of energy used to ablate and treat varicose veins include laser or RF energy. For this type of treatment, the energy is delivered by an elongated energy delivering member, such as an optical fiber or RF probe, that is percutaneously inserted into the diseased vein prior to energy delivery. An introducer catheter or sheath may first be inserted and advanced to within a few centimeters of the saphenous-femoral junction of the greater saphenous vein. Once the introducer catheter is properly positioned, elongated energy delivering member is inserted into the lumen of the catheter or sheath and advanced until elongated energy delivering member is in place at the treatment site. Next, tumescent anesthesia is injected several times along the diseased vein segment. The tumescent injections can be used to perform several functions. The anesthesia inhibits pain caused from the application of thermal energy to the vein. The tumescent injection also provides a barrier between the vessel and the adjacent tissue and nerve structures, which restricts radiant heat damage to within the vessel and prevents non-target tissue damage. The tumescent injection also compresses the vein by reducing its diameter which increases the success of the procedure.

The use of tumescent anesthesia may lead to several problems. The first problem with tumescent anesthesia is it's often the longest procedural step in the treatment, usually requiring two medical professionals to perform. Depending on vein length and location, the administration of tumescent anesthesia may take up to 15 minutes or more. Multiple tumescent anesthesia injections are often required along substantially the entire length of the target vein segment. Another problem with the delivery of tumescent anesthesia is that the multiple "needle-stick" injections can be painful and cause discomfort to the patient. These "needle-stick" injections may scar, and can lead to complications, such as inadvertent needle contact with non-targeted structures, such as nerves, or lead to possible infection. In addition, the needle-sticks can be difficult to control, and the vein is sometimes perforated which enhances bruising. Also, the tumescent anesthesia sometimes insufficiently surrounds the vein and pain and parasthesia can result. An object of this invention is to provide a treatment for varicose veins without requiring the use of tumescent anesthesia.

Plasma, often referred to as the fourth state of matter, is defined as a specific state of matter of electrically charged particles, consisting of, but not limited to, ions, charged molecules, electrons, sub-atomic particles, and excited atoms. Plasma is generally regarded by scientists and those skilled in the art as a separate state of matter different from gas, liquid, or solid.

Non-thermal plasma is a form of plasma existing at low temperatures, such as room temperature, is defined when electrons achieve the energy level normally found in all components of thermal plasma. Non-thermal plasma produced by this invention may be of a temperature below the pain threshold of the surrounding tissue which is roughly between about 45-50° C., and this non-thermal plasma temperature is well below that of current energy-based treatment methods, such as laser which sometimes exceed over 1000° C. immediately adjacent to the fiber emitting tip.

Recently, non-thermal or low-thermal plasmas have been used by those in the art for various procedures. Such non-thermal or low-thermal plasmas are also sometimes called cold plasma or non-equilibrium plasma. Uses of non-thermal plasmas in the art include sterilization of foodstuffs and treatment of topical skin surfaces of patients. An object of this invention is to use either thermal plasma or non-thermal plasma in a novel way for the treatment of hollow anatomical structures within the body.

FIELD OF THE INVENTION

This invention relates to occlusion of hollow anatomical structure by inserting occluding device or material by use of plasma to facilitate occlusion.

SUMMARY OF THE DISCLOSURE

Figure 1:
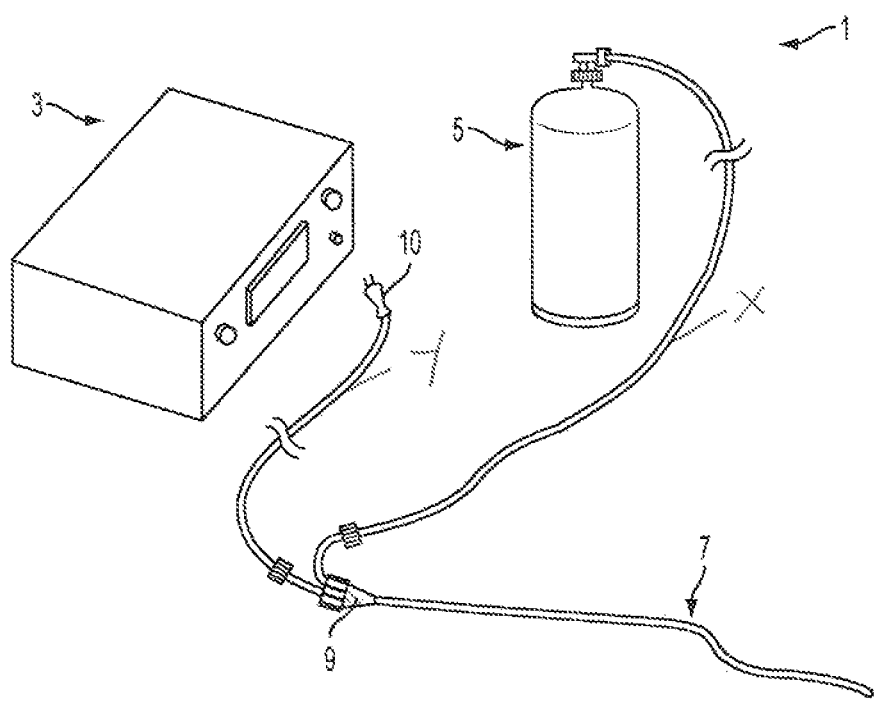
FIG. 1 is a schematic diagram of one exemplary embodiment of the treatment system described herein showing an energy generator, container, and delivery catheter.

A medical device and method of use for treating a hollow anatomical structure comprising a tubular delivery device comprising a tubular body, a hub, and a distal end. The tubular body device includes a longitudinal fluid delivery channel and an exit port near the distal end. The system also comprises a container having pre-plasma matter being operatively coupled to the hub and at least one energy-emitting element operatively coupled near the distal end of the tubular delivery device. The energy-emitting element is operatively connected to energy source.

An endoluminal treatment method comprising inserting into an anatomical lumen a catheter having an energy delivery emitting element and catheter lumen. Delivering pre-plasma matter through the catheter lumen and activating the energy delivery emitting element to cause the pre-plasma matter to be converted to create plasma from the pre-plasma matter. The creation of plasma causing shrinkage and eventual collapse of the endoluminal lumen.

Other advantages of the apparatus and method of the present invention will become more readily apparent in view of the following detailed description of the invention and accompanying drawings.

DETAILED DESCRIPTION

A treatment device and method of using plasma to disrupt the endothelial cells or intimal wall of a hollow anatomical structure will now be described. Plasma may be created by altering or charging ions, electrons, neutrons, atoms or other molecular structures of a gas, liquid, or solid by either reducing or increasing the number of positive ions and/or negative electrons. This gas, liquid, or solid may be defined as pre-plasma matter. Altering pre-plasma matter into plasma may be done by applying various energy forms to the pre-plasma matter. The altered or charged particles of the plasma created by this device will attempt to stabilize and reach a state of molecular equilibrium by attracting complementarily charged cellular components present in the cells lining the target hollow anatomical structure. As a result, this device will create plasma, as described below, which reacts at a molecular level with the cells lining the target hollow anatomical structure causing these cells to undergo an ionic or atomic transformation, reorganization or denaturement resulting in eventual cell death and occlusion. Plasma created by this device may be either thermal plasma, low-temperature plasma, or non-thermal or cold plasma.

An advantage of using thermal plasma to treat a hollow anatomical structure is creating an ablation effect during treatment near the treatment zone. This means in addition to altering or denaturing the molecular structure of the endothelial cells or intimal wall of the treatment zone using plasma there is also a thermal ablation effect similar to laser or RF ablation at or near the treatment zone. An advantage of using low-temperature, non-thermal or cold plasma to treat a hollow anatomical structure is to sustain normal body temperatures at or near the treatment zone avoiding radiating thermal damage to unintended tissue at or surrounding the treatment zone. An additional advantage of using non-thermal plasma with device is tumescent anesthesia may not be required pre-opt. For example, non-thermal plasma may be used for the treatment of varicose veins without the use of tumescent anesthesia for several reasons. First, non-thermal plasma may be produced at temperatures lower than the pain threshold so there is no need to use an anesthetic agent for numbing purposes. Also, since non-thermal plasma will not create radiating heat or rise in temperature of surrounding tissue, perforations of the vessel caused by high heat will not occur. Additionally, because there may be little to no radiating heat created by non-thermal plasma there is no need to create a barrier preventing thermal damage to non-target adjacent structures that would otherwise need to be protected by tumescent anesthesia. Furthermore, the plasma bolus expands to fill the lumen of the vessel, as described in more detail below, so there will no need to reduce the vessel diameter required with conventional techniques.

Examples of hollow anatomical structures treated with device 1 may include, but not limited to, veins, varicose veins, arteries, hemorrhoids, arterio-venous malformations (AVM), vascular or nonvascular ducts, esophagus, gastro-intestinal pathways, urethra, air passages and fallopian tubes.

FIG. 1 represents one embodiment of the treatment device 1 consisting of a container 5, an energy generator 3, and a delivery catheter 7. The delivery catheter 7 provides a fluid channel for delivery of the pre-plasma matter from the container 5 via tubing X to the treatment site at the distal section of the catheter 7. The energy generator 3 is connected to the catheter via tubing Y to provide plasma-activating energy to the distal section of the catheter where the pre-plasma material has been delivered.

Examples of delivery catheter 7 that can be used include, but not limited to, standard catheters known in the art, sheaths, needles, cannulas, and other tubes known in the art. As explained in more detail below, the delivery catheter 7 includes a fluid delivery channel for delivery of the pre-plasma matter to the targeted site and an energy-delivery element for creation of plasma.

The container 5 houses pre-plasma matter being used to generate the plasma mass. Examples of such pre-plasma matter include, but not limited to, nitrogen, argon, xenon, krypton, helium, neon, and carbon monoxide, and/or any combination of such gasses. The container 5 may be a reusable tank, as known in the art, a disposable single-use canister, a plunger syringe as known in the art, or any other device capable of holding or delivering pre-plasma material to the target site through the delivery catheter 7. The container 5 may be pre-pressurized so that when the container 5 is opened or activated high pressure forces pre-plasma matter to escape from the container 5 and be delivered to the catheter 7 through hub 9. Alternatively, the container 5 may be a standard plunger type syringe as known in the art, or another container or vessel that can become pressurized during use. Also, the container 5 may include a power injectable component so that when activated it delivers the pre-plasma matter at high pressures. High pressures may be required to achieve proper plasma cloud formation and prevent dilution of pre-plasma matter. The container 5 may be releasably coupled to the catheter 7 via tubing X which connects to catheter hub 9, for delivery of the pre-plasma matter through the catheter lumen. The delivery amount of pre-plasma matter from the container 5 may be controlled by the user during treatment. For example, the user may control the flow pressure or the flow rate with either a switch, button or other mechanism which can turn off the fluid flow. Also, the flow fluid may be controlled in such a way that the pre-plasma matter is delivered using constant, low pressure flow, high pressure flow, pulsed etc. Additionally, the system may comprise a mechanism to control delivery of pre-plasma matter and eliminate the possibility of migration of any air or gas bubbles delivered into unintended areas of the body.

The energy generator 3 may include, but is not limited to, an RF or laser generator, an electromagnetic generator, direct current generator, such as an electroporation generator, an energetic photon generator, magnetic pulse generator, microwave or any other device capable of generating an energy field to excite the pre-plasma matter sufficiently to convert the matter to plasma.

The connection 10 between catheter 7 and the energy generator 3 will depend on the type of energy used. For example, if laser energy is being used the energy generator 3 may be a diode laser and the connector 10 may be a SMA type connector.

Figure 2A:
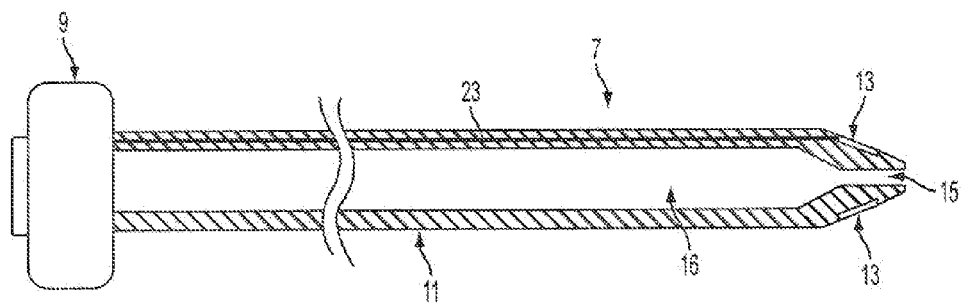
FIG. 2A is a longitudinal sectional view of one exemplary embodiment of a delivery catheter.

FIG. 2A represents one embodiment of the delivery catheter 7 comprising a hub 9, tubular body 11 comprising a longitudinal lumen 16 having an end hole 15, energy conduit 23, and at least one energy emitting element 13 positioned near the distal end of the catheter 7. Tubular body 11 may be made of known materials used for catheters. The energy conduit 23 may be disposed within wall of the tubular body 11. Conduit 23 provides a means for connecting the energy emitting element 13 to the external energy generator 3. The type of energy conduit 23 will depend on the form of energy being used by device, for example if laser energy is being used the energy conduit 23 will likely be an optical fiber. The energy conduit 23 may also be a wire cable able to conduct various forms of energy. Alternatively, no energy conduit 23 may be required if the energy element 13 is wirelessly connected to the energy generator 3, using any suitable wireless protocol including IEEE 802.11 (a, b, g, or n) and any other suitable protocols used in the art.

Energy emitting element 13 may be an RF electrode, electroporation electrode, multiple electrodes, microwave antenna, ultrasound transducer, piezoelectric crystals, optical fiber, or any other element capable of emitting or creating an energy field in or near the treatment zone. The energy conduit 23 and energy emitting element 13 can either be embedded into the wall of the tubular body 11 or be an independent device freely moveable relative to catheter 7 and either co-axially disposed within the lumen 16 of the catheter (not shown) or coaxially disposed outside the tubular body 11 (not shown). Pre-plasma material is delivered through end hole 15.

Figure 2B:
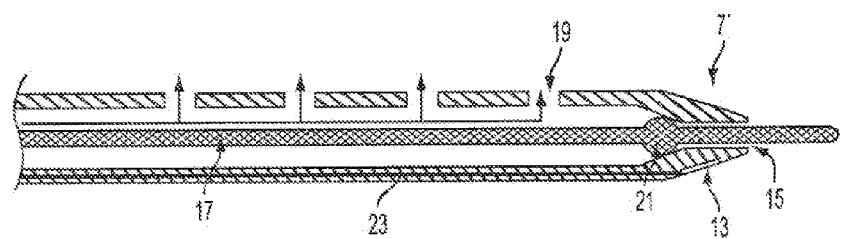
FIG. 2B is a longitudinal sectional view of another exemplary embodiment of the catheter with an occluding wire element.
Figure 3A:
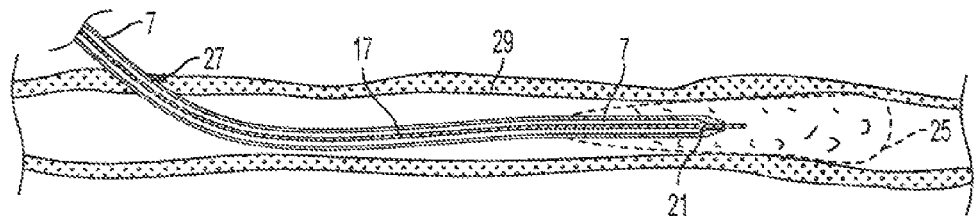
FIG. 3A illustrates a method of using any of the catheter devices described herein, at the beginning of treatment, creating plasma cloud within a vessel.
Figure 3B:
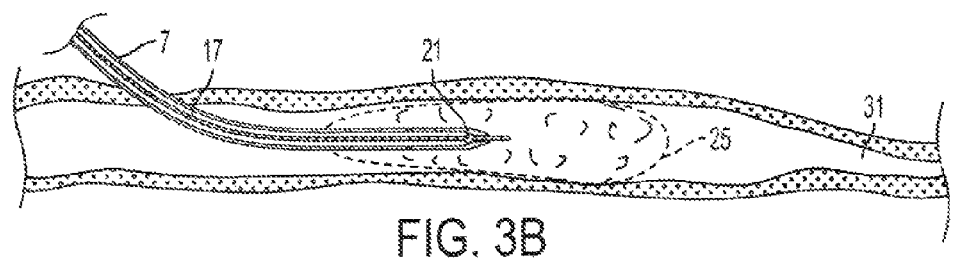
FIG. 3B illustrates continuation of treatment, with the catheter being withdrawn as pre-plasma continues to be delivered to the vessel.
Figure 3C:
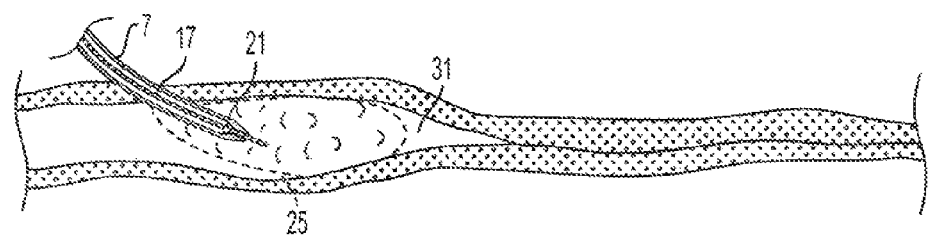
FIG. 3C illustrates continuation of treatment, as the previously treated segment begins to collapse.
Figure 3D:
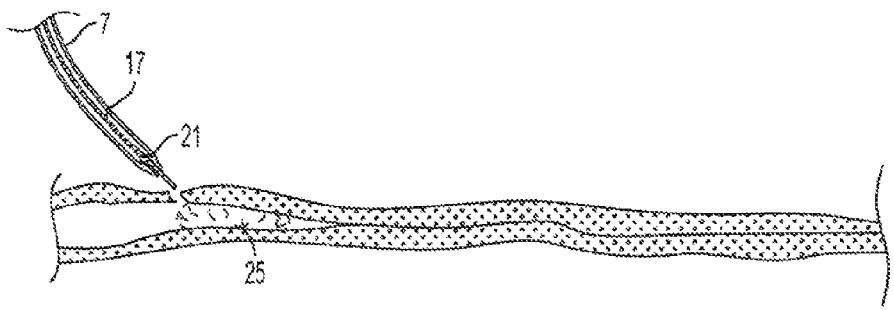
FIG. 3D illustrates the end of treatment as the catheter is withdrawn from the vessel.
Figure 4:
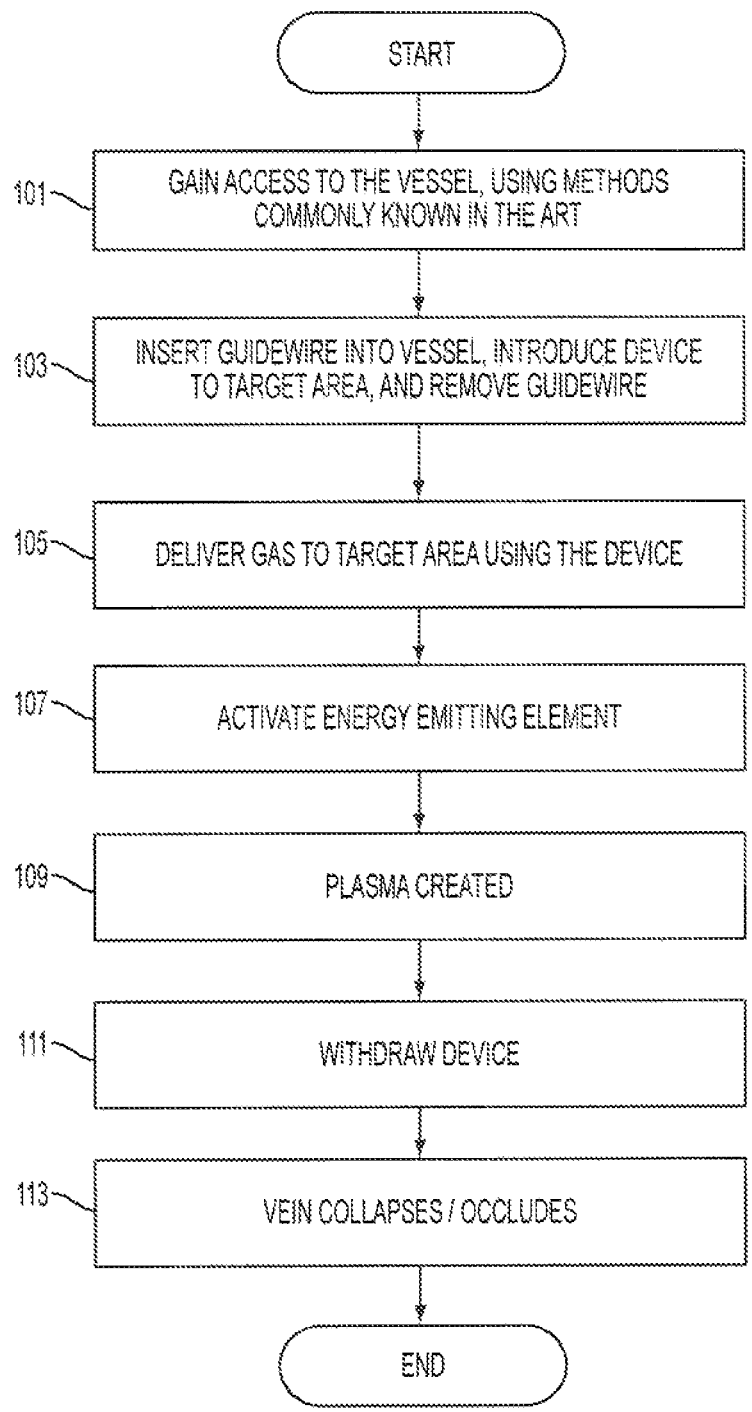
FIG. 4 is a flow chart of one exemplary embodiment of the method of treatment described herein.

FIG. 2B represents a second embodiment of the catheter 7 comprising a plurality of side wall openings 19 along distal end of the catheter 7. The side wall opening 19 may include either pressure responsive slits or port openings with predetermined diameters. Such pressure responsive slits are described in detail in U.S. Pat. No. 5,267,979, which is incorporated herein by reference. An advantage of having a plurality of side wall opening 19 along distal end of catheter 7 is pre-plasma matter may be delivered (shown by the arrows in FIG. 2B) along a larger segment increasing the size of the treatment zone. Increasing the size of the treatment zone this may cut down on overall procedure time because more pre-plasma matter can be delivered at one time.

An end-hole occluding wire 17 or other occluding member may be used to occlude 21 the end hole 15 of the catheter 7 during delivery of pre-plasma matter. Occluding the end hole 15 during deliver is advantageous because the pre-plasma matter may be uniformly delivered from the catheter 7 at equal pressures along all the side openings 19. The occluding wire 17 may be a standard guidewire as known in the art with an occluding ball 21 near its distal end, as disclosed in U.S. Pat. No. 6,283,950, which is incorporated herein by reference. The occluding wire 17 assembly may be left in catheter 7 during treatment. The catheter 7 of this embodiment may include at least one energy emitting electrode 13 positioned near the distal end of the catheter 7. Alternatively, the catheter 7 may have several energy emitting electrodes 13 all along the distal end of the catheter 7 near the side opening 19 to provide for simultaneously treatment of longer vein segments.

This embodiment may have an energy conduit 23 coaxially disposed within tubular body 11 as described above, or alternatively, the energy emitting element 13 and energy conduit 23 may be combined with or replace the end-hole occluding wire 17. For example, if laser energy is being used the end-hole occluding wire 17 may be an optical fiber (not shown) or other energy source coaxially disposed in lumen 16 and independently movable from the catheter 7. The distal end of the optical fiber may be sized so to occlude end-hole 15 of catheter 7 and perform essentially the same function as end-hole occluding wire 17.

FIGS. 3A-D and FIG. 4 refer to the method of using device 1 described above. As the initial step, a physician gains access 101 using techniques earlier described and known in the art through insertion point 27 of target vessel wall 29. A guidewire may next be inserted into the vessel lumen 31. Catheter 7 is introduced to the vessel over guidewire or occluding element 17 and advanced through the vessel until the distal section of catheter 7 is located at or near the treatment zone 103 before removing the guidewire. Alternatively, if an occluding ball wire 17 is being used the occluding ball wire 17 element may be left in lumen of catheter 7 during treatment.

After the catheter is connected to the container and energy source as previously describe, the pre-plasma matter is released from the container 5 by the user. The user may have the ability to control the pressure or rate in which the pre-plasma matter is delivered or injected during treatment. For example, if container 5 is a syringe the user may control delivery pressure of the pre-plasma matter by altering the amount of force exerted onto the plunger. Controlling the injection pressure of the pre-plasma matter may help in creating a plasma cloud 25 optimized to contact a vessel wall that contacts the vessel wall, as described below, so providing the user the ability to control and change injection pressures may be an advantage of this device. The pre-plasma matter exits the container 5 travels through tubing X through hub 9 and into the lumen 16 of tubular body 11, finally exiting through the end hole 15 of the catheter 7 or alternatively through the plurality of side wall openings 19 into the target lumen 31.

If the pre-plasma matter is in a gaseous or liquid state it may exit or be forced from catheter lumen 16 under pressure creating a cloud, plume or bolus of pre-plasma matter at the treatment zone. The plasma cloud 25 displaces any blood or other fluid within the anatomical lumen proximate to the distal section of the catheter 7. Is it the delivery of the pre-plasma which causes the displacement. As a result of this displacement, the pre-plasma matter is not diluted by blood flow or other luminal fluid. The displacement reduces chances of pre-plasma migration because the pre-plasma matter does not mix with the blood or other luminal fluid. In addition, the displacement of blood in the target or treatment area allows the plasma matter to directly contact and react with the endothelial cells or intimal wall of a hollow anatomical structure being treated. If the pre-plasma matter being delivered is in a liquid state then to prevent the liquid from flowing into the deep venous system or other non-targeted area, the device may optionally include a distal occluding element (not shown), such as an occluding balloon, as is known in the art, to prevent unwanted liquid migration.

After device 1 is in place at or near the treatment zone, the physician begins treatment by slowly retracting the device in a proximal direction. The pre-plasma matter may be delivered as a single bolus, or alternatively as a continuous bolus during withdrawal. Other pre-plasma matter delivery patterns are contemplated, including, but not limited to, segmental length delivery, pulse mode, spot ablation, or in a continuous mode.

After the delivery of pre-plasma matter, user may activate 107 the energy generator 3 to transmit energy to the energy emitting element 11. Alternatively, the energy generator 3 may be activated prior to the delivery of pre-plasma material to the vessel. Energy emitted from device 1 reacts with ions in pre-plasma matter bolus being delivered from catheter lumen 16 creating 109 a cloud 25 of plasma at or near the treatment zone. In one embodiment the plasma cloud 25 consists of non-thermal plasma and therefore has no thermal footprint and does not raise the temperature of tissue at or near the treatment site. In another embodiment, the plasma cloud 25 consists of low-level thermal plasma which may be below the pain threshold and may slightly increase temperature at or near the treatment site, but of insufficient temperature to cause damage to surrounding or adjacent non-targeted structures. In yet another embodiment the plasma cloud 25 consists of thermal plasma and an ablation zone is created near or at the treatment site. The charged matter of the plasma cloud 25 will interact with the cellular lining of target vessel 29 to actively induce cell death. For example, the individual ions within the plasma cloud 25 will attempt to stabilize by attracting complementarily charged cellular components present in the cells lining the vessel wall 29.

After the desired segment has been treated, the catheter 7 is moved in a proximal direction to the next treatment site until the entire vessel segment has been treated. As plasma cloud 25 is delivered and catheter 7 withdrawn 111 the inner cellular wall begins to break down as the atomic bonds of the cells lining the vessel wall 29 eventually denature or die, total vein collapse or occlusion 113. The method may include segmental treatment in which a bolus of pre-plasma material is delivered followed by energy activation and plasma creation. Once plasma is created the device is withdrawn and the next segment is treated by delivering another bolus and re-activating the energy delivery element. Alternatively the method may include constant and continual pre-plasma delivery with continuous energy during pull back of the catheter.

As the plasma interacts with the inner wall of the vessel or other duct, the damage caused to the vessel lining causes the vessel to shrink and eventually collapse.

If the device is being used to treat varicose veins, the blood from the vein being treated may either be removed prior to treatment or remains in the vein during the treatment. In the embodiment when blood remains in the vessel no pre-plasma matter may be required because the molecules found in blood may be used to create the plasma cloud 25.

The systems, devices, and methods described herein are not limited to use of a catheter for delivery of pre-plasma matter and energy. In one embodiment as an example, a short varicose vein segment such as a perforator can be treated using a short needle.

In another embodiment, the pre-plasma matter may be activated by an energy emitting element placed on the surface of the skin, such as a standard or High-Frequency Ultrasound (HIFU) transducer or other ultrasound emitting transducer. Either unfocused or focused ultrasound may be used to activate the plasma mass. For example, the device of this embodiment may comprise a beacon at or near the distal end of a delivery catheter and the beacon can be made of piezoelectric crystals or another material capable of receiving ultrasound waves. The system of this embodiment may include transmitting focused ultrasound waves capable of exciting pre-plasma matter into a plasma cloud 25 as described above.

In yet another embodiment, the invention may comprise a procedural kit containing a catheter, energy-emitting element(s), and a single-use, disposable canister containing pre-plasma matter. In another aspect, the kit may include a disposable canister which is provided empty and is subsequently filled by a user with desired pre-plasma matter prior to treatment. In another aspect, a portable canister capable of being refilled, satirized and reused is provided.

In yet another embodiment the device comprises an elongated element with an energy conduit or plasma forming element located near distal end of the elongated element. In this embodiment neither gas nor liquid is used to create a plasma treatment zone. The energy conduit or plasma forming element will be able to create a high density mass or area of excited atoms, ions, radicals and free electrons without the use of pre-plasma matter, and may be used to modify and/or destroy biological tissue in a body vessel. An advantage of using an energy conduit or plasma forming element without pre-plasma matter is that the device may be less expensive to make, there may be a lower risk of complications because less foreign material will be injected into the patient's body, size of the device may be smaller, and less complicated procedure. Such an energy conduit or plasma forming element may include, but is not limited to, all energy sources identified above, any energy capable of creating plasma, ultrasound, and microwave. The energy conduit or plasma forming element may be able to create plasma in multiple temperature ranges, including but not limited to thermal plasma, non-thermal plasma, and specifically plasma below the pain threshold of 45-50 degrees Celsius.

Alternatively, another embodiment includes a mechanism in which plasma can be created by converting pre-plasma matter at the proximal end of the delivery catheter 7. For this embodiment the energy emitting element may be located near the proximal end of the delivery catheter 7, such as on the hub 9. Plasma is created near the proximal end of the catheter 7 and then delivered through delivery catheter 7 to the treatment site.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". The words "including" and "having," as used herein including the claims, shall have the same meaning as the word "comprising." Those familiar with the art can recognize other equivalents to the specific embodi-

The invention claimed is:

1. An endoluminal treatment method comprising:
   inserting into an anatomical lumen a catheter having at least one energy emitting element near the distal end of the catheter and a catheter lumen;
   delivering pre-plasma matter in a gaseous state through the catheter lumen;
   activating the energy emitting element to create plasma from the pre-plasma matter wherein the plasma causes shrinkage of the anatomical lumen.

2. A method of claim 1, wherein the step of delivering the pre-plasma matter further comprises delivering the matter through an end hole of the catheter.

3. A method of claim 2, wherein the step of delivering the pre-plasma matter further comprises delivering the matter through at least one side opening in the catheter.

4. A method of claim 3, prior to delivering pre-plasma matter, further comprising inserting an occluding ball wire into the catheter lumen.

5. A method of claim 1, wherein the step of inserting includes the energy emitting element comprising an optical fiber.

6. A method of claim 1, wherein the step of inserting includes the energy emitting element comprising an electrode.

7. A method of claim 6, wherein the electrode further comprises a radiofrequency electrode.

8. A method of claim 1, wherein the step of inserting includes the energy emitting element comprising a beacon capable of receiving ultrasound waves.

9. An endoluminal treatment method comprising:
   inserting into a varicose vein a catheter having a lumen, an energy emitting element located within a container containing the pre-plasma matter;
   activating the energy emitting element to create plasma from pre-plasma matter;
   delivering plasma matter through the catheter lumen wherein the plasma causes shrinkage of the anatomical lumen.

10. A method of claim 9, wherein the step of inserting further comprises the energy emitting element is positioned near the proximal end of the catheter.

11. A method of claim 9, wherein the step of delivering includes the pre-plasma matter in a gaseous state.

12. A method of claim 9, wherein the step of delivering includes the pre-plasma matter in a liquid state.

13. A method of claim 9, wherein the step of delivering the pre-plasma matter further comprises delivering the matter through an end hole of the catheter.

14. A method of claim 9, wherein the step of delivering the pre-plasma matter further comprises delivering the matter through at least one side opening in the catheter.

15. A method of claim 14, prior to delivering pre-plasma matter, further comprising inserting an occluding ball wire into the catheter lumen.

16. An endoluminal treatment method comprising:
   inserting into an anatomical lumen a catheter having at least one energy emitting element near the distal end of the catheter and a catheter lumen; wherein the at least one energy emitting element is comprised of an electroporation electrode or a microwave antenna;
   delivering pre-plasma matter through the catheter lumen;
   activating the energy emitting element to create plasma from the pre-plasma matter wherein the plasma causes shrinkage of the anatomical lumen.

* * * * *